(12) United States Patent
Shin et al.

(10) Patent No.: US 10,041,031 B2
(45) Date of Patent: Aug. 7, 2018

(54) APPARATUS AND PROCESS FOR CONTINUOUS SACCHARIFICATION OF MARINE ALGAE AND CELLULOSIC BIOMASS

(71) Applicants: BIOL SYSTEMS CO., LTD., Jeollanam-do (KR); DAEWOO SHIPBUILDING & MARINE ENGINEERING CO., LTD., Seoul (KR)

(72) Inventors: Myung Kyo Shin, Jeollanam-do (KR); Dong In Jeong, Gwangju (KR); In Sik Kim, Seoul (KR); Dongjoong Im, Seoul (KR)

(73) Assignees: Biol Systems Co., Ltd., Jeollanam-do (KR); Daewoo Shipbuilding & Marine Engineering Co., Ltd., Seoul (KR)

( * ) Notice: Subject to any disclaimer, the term of this patent is extended or adjusted under 35 U.S.C. 154(b) by 740 days.

(21) Appl. No.: 14/905,878

(22) PCT Filed: Oct. 29, 2012

(86) PCT No.: PCT/KR2012/008915
§ 371 (c)(1),
(2) Date: Jan. 18, 2016

(87) PCT Pub. No.: WO2013/062382
PCT Pub. Date: May 2, 2013

(65) Prior Publication Data
US 2016/0152937 A1 Jun. 2, 2016

(30) Foreign Application Priority Data
Oct. 27, 2011 (KR) .................. 10-2011-0110789

(51) Int. Cl.
*B01J 19/18* (2006.01)
*C08B 37/00* (2006.01)
(Continued)

(52) U.S. Cl.
CPC .......... *C12M 23/58* (2013.01); *B01J 19/1862* (2013.01); *C08B 37/0003* (2013.01);
(Continued)

(58) Field of Classification Search
CPC .... B01J 2219/00164; B01J 2219/00162; B01J 2219/187; B01J 2219/00166;
(Continued)

(56) References Cited

U.S. PATENT DOCUMENTS 3,024,158 A * 3/1962 Grangaard ........... D21C 9/1068
162/17
3,305,466 A * 2/1967 McCoy .................... B01J 15/00
204/164

(Continued)

FOREIGN PATENT DOCUMENTS

KR 10-2001-0077869 A 8/2001
KR 10-2010-0093253 A 8/2010
(Continued)

OTHER PUBLICATIONS

Int'l. Search Report of PCT/KR2012/008915 dated Mar. 25, 2013.

*Primary Examiner* — Joseph Drodge
(74) *Attorney, Agent, or Firm* — Greer, Burns & Crain, Ltd.

(57) ABSTRACT

The present disclosure relates to an apparatus and process for continuous saccharification of marine algae and cellulosic biomass.

12 Claims, 4 Drawing Sheets

(51) Int. Cl.
  *B01F 3/12* (2006.01)
  *C12M 1/00* (2006.01)
  *C12M 1/02* (2006.01)
  *C12M 1/34* (2006.01)

(52) U.S. Cl.
  CPC ............ *C12M 27/00* (2013.01); *C12M 29/06* (2013.01); *C12M 41/40* (2013.01); *B01J 2219/00094* (2013.01); *B01J 2219/00162* (2013.01); *B01J 2219/00164* (2013.01); *B01J 2219/00166* (2013.01); *B01J 2219/187* (2013.01)

(58) Field of Classification Search
  CPC .............. B01J 2219/00094; B01J 19/18; B01J 19/1818; B01J 19/1862; B01J 19/242; B01J 19/245; C12M 23/58; C12M 41/40; C12M 27/00; C12M 27/02; C12M 27/06; C12M 29/06; C08B 37/00; C08B 37/0003; C13B 40/00; C13B 99/00
  USPC ......... 127/2, 9, 42, 46.1; 366/144, 145, 280; 422/600, 624, 630, 632, 633, 642, 650, 422/659, 224, 225, 229
  See application file for complete search history.

(56) References Cited

U.S. PATENT DOCUMENTS

| | | | | |
|---|---|---|---|---|
| 3,446,664 | A * | 5/1969 | Miyazaki | B01J 16/00 127/1 |
| 8,123,864 | B2 * | 2/2012 | Christensen | C08B 37/0057 100/38 |
| 8,968,515 | B2 * | 3/2015 | Balan | C12P 7/10 127/2 |
| 2010/0209976 | A1 | 8/2010 | Cho et al. | |
| 2010/0311157 | A1 | 12/2010 | Van Alstyne et al. | |
| 2011/0027827 | A1 | 2/2011 | Chi et al. | |
| 2012/0156744 | A1 * | 6/2012 | Macdonald | C02F 3/286 435/155 |

FOREIGN PATENT DOCUMENTS

| | | |
|---|---|---|
| KR | 10-2011-0046090 A | 5/2011 |
| WO | WO 2011/088422 A2 | 7/2011 |

* cited by examiner

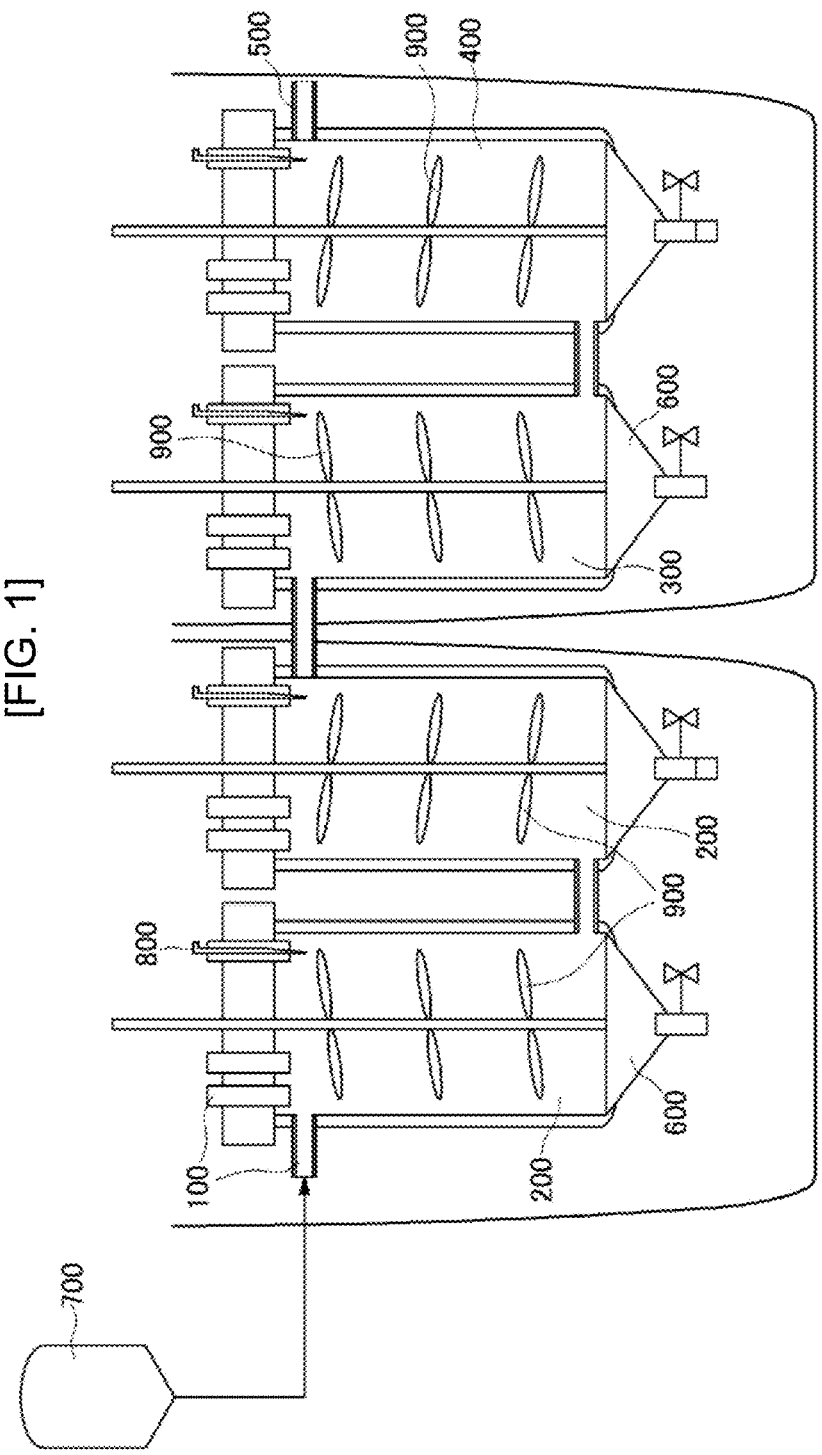
[FIG. 1]

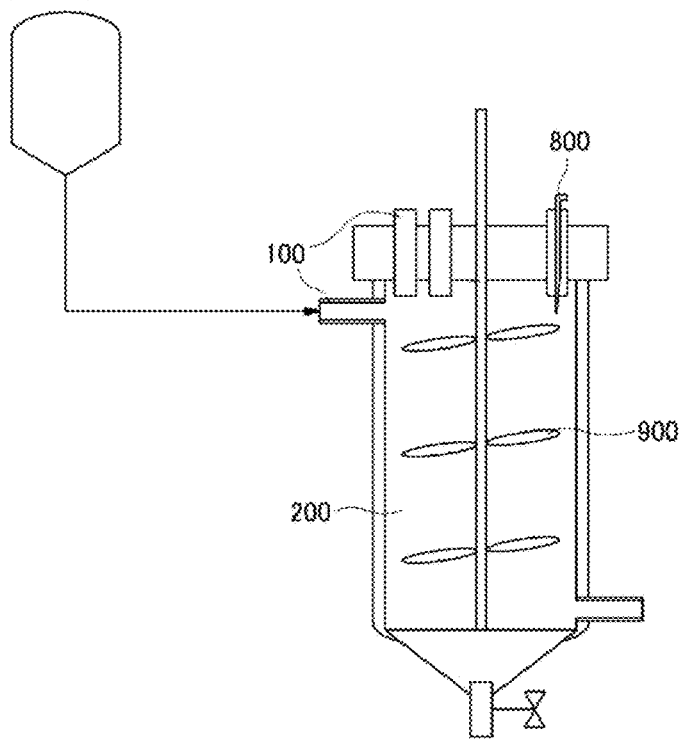
[Fig. 2]
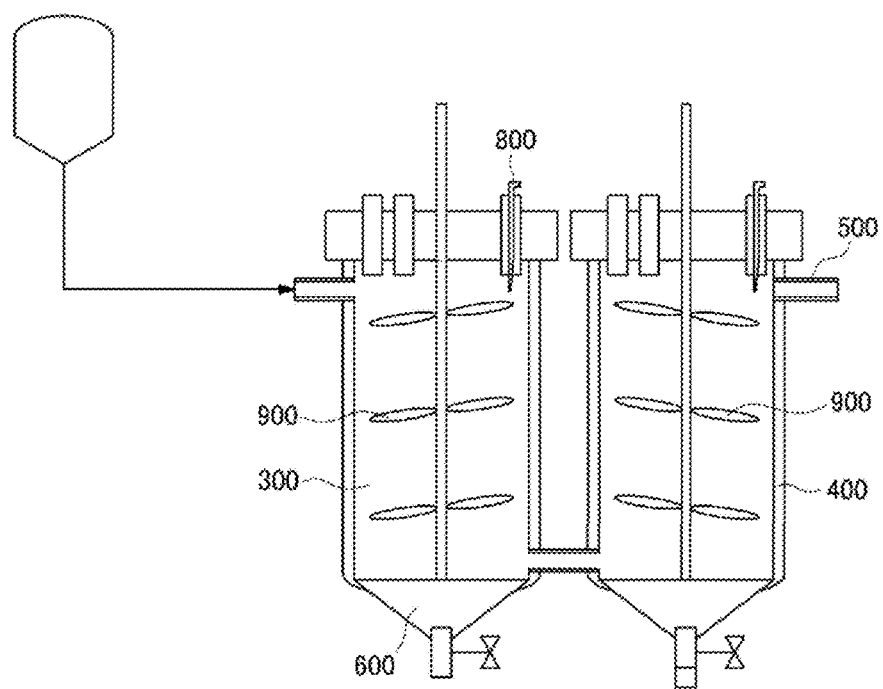
[Fig. 3]

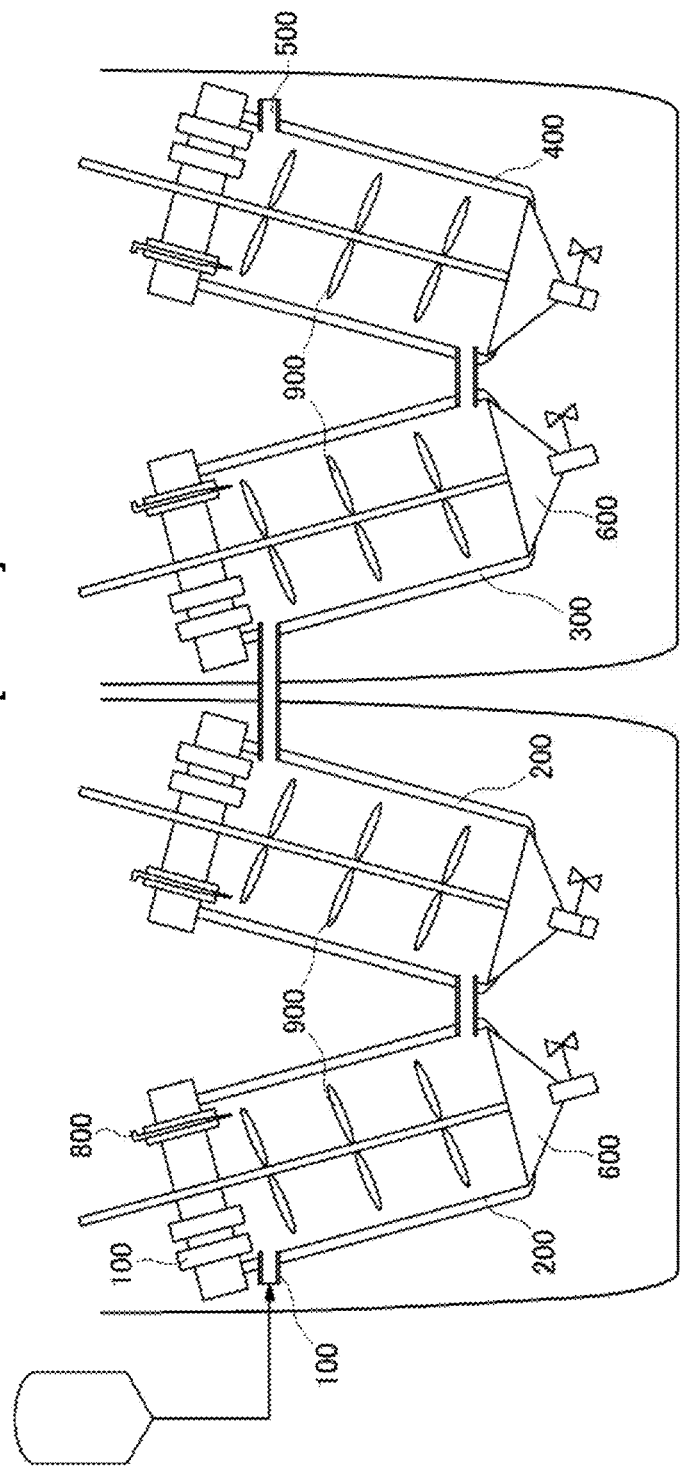
[FIG. 4]

[Fig. 5]
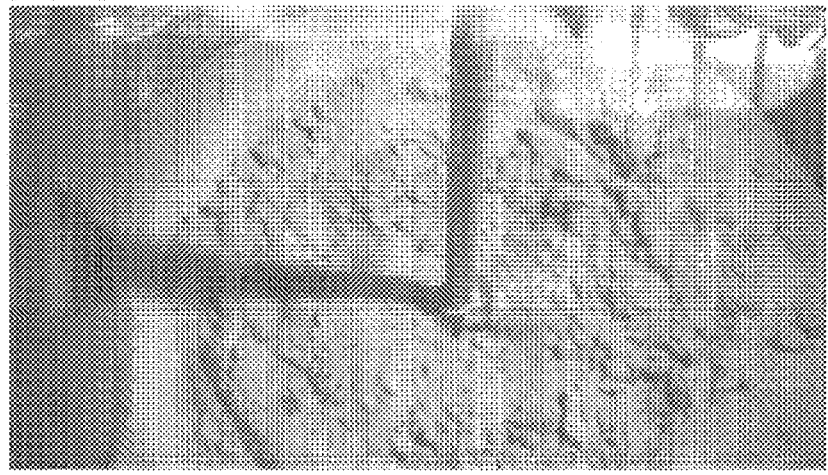
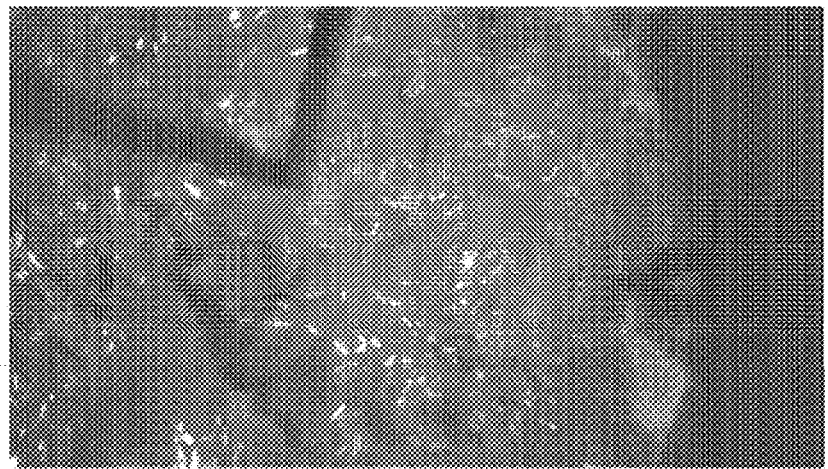

APPARATUS AND PROCESS FOR CONTINUOUS SACCHARIFICATION OF MARINE ALGAE AND CELLULOSIC BIOMASS

TECHNICAL FIELD

The present disclosure relates to a apparatus and process for continuous saccharification of marine algae and cellulosic biomass.

BACKGROUND ART

Biomass is a general term to refer to all organic materials currently being used as energy sources including dedicated energy crops and trees, agricultural products and forage crops, agricultural wastes and residues, forest product wastes and wood chips, water plants, excretion of animals, industrial wastes including municipal wastes, and other renewable organic materials extracted from the above-described wastes. The biomass is a huge energy storage that keeps solar energy. If it is possible to effectively use the biomass, a current energy crisis caused by overuse of fossil fuels can be solved easily. Since the biomass is cultured to produce energy to be used as much as needed, it is possible to prevent excessive accumulation of carbon dioxide in the air. Therefore, it may be possible to solve global warming being currently brought up as a very serious problem.

Bioethanol as one of alternative energy sources using the biomass is extracted from plants such as sugar cane, corn, and the like and can be used as an automotive fuel in a combined manner with gasoline or solely. Therefore, the bioethanol has drawn attention as a representative renewable energy source together with biodiesel. Biomass ethanol is described in documents as follows: DiPardo, Journal of Outlook for Biomass Ethanol Production and Demand (EIA Forecasts), 2002; Sheehan, Biotechnology Progress, 15 8179, 1999; Martin, Enzyme Microbes Technology, 31 274, 2002; Greer, BioCycle, 61-65, April 2005; Lynd, Microbiology and Molecular Biology Reviews, 66 3, 506-577, 2002; and Lynd et al in "Consolidated Bioprocessing of Cellilosic Biomass: An Update," Current Opinion in Biotechnology, 16 577-583, 2005.

However, as the bioethanol has drawn attention as alternative energy, a demand for corn, sugar crane, and wheat as sources of the bioethanol has been sharply increased, which becomes a factor of a sharp rise in crop prices. Accordingly, a method of obtaining bioethanol from crops causes the above-mentioned problem of a sharp rise in crop prices and cannot avoid criticism that such crops should be supplied to many starving people as food. Therefore, a global bioethanol market has turned its attention from crops to wood. However, there is no way of making a breakthrough since the wood needs to go through a complicated process of removing lignin or the like.

Accordingly, recently, marine algae have drawn attention as a source of the bioethanol. Since the marine algae have a high growth rate, it is possible to mass-produce them without any fertilizer or agricultural water. Further, since the marine algae are rich in various sugar components and alginic acid, they are suitable to be converted into energy. Furthermore, the marine algae are about 1.5 to 2 times richer in carbohydrates than wood.

Moreover, since the marine algae have a less dense structure than lignin, as compared with conventional biomass, it is relatively easy to perform saccharification on the marine algae, resulting in a great amount of output. Besides, since relatively abundant marine resources can be utilized, the marine algae have great potential.

DISCLOSURE OF INVENTION

Technical Problem

The present disclosure provides a apparatus and process for continuous saccharification of marine algae and cellulosic biomass and the apparatus and process can saccharify biomass source effectively.

However, the problems to be solved by the present disclosure are not limited to the above description and other problems can be clearly understood by those skilled in the art from the following description.

Solution to Problem

In accordance with a first aspect of the present disclosure, there is provided an apparatus for continuous saccharification of marine algae and cellulosic biomass, the apparatus comprising a source input unit; a reactor; a reaction unit including a downward reactor and an upward reactor; a reactant liquid discharge unit; and a deposit removal unit.

In accordance with an illustrative embodiment of the present disclosure, the source includes marine algae including macro-algae, terrestrial cellulosic biomass, or the combination thereof.

In accordance with an illustrative embodiment of the present disclosure, the marine algae include marine algae containing water or marine algae from which water is removed by a dehydration process.

In accordance with an illustrative embodiment of the present disclosure, the source input unit further includes an agitator.

In accordance with an illustrative embodiment of the present disclosure, the reactor comprises a spraying device, a driving unit, and a pressure control device.

In accordance with an illustrative embodiment of the present disclosure, the spraying device is configured to directly inject high-pressure steam into the reactor.

In accordance with an illustrative embodiment of the present disclosure, a plurality of the reaction unit is included.

In accordance with an illustrative embodiment of the present disclosure, the downward reactor and the upward reactor further include a impeller.

In accordance with an illustrative embodiment of the present disclosure, a slope of the impeller is adjusted depending on a reaction direction of the downward reactor and the upward reactor.

In accordance with an illustrative embodiment of the present disclosure, the source is mixed with a reaction catalyst in the reactor.

In accordance with an illustrative embodiment of the present disclosure, the reaction catalyst includes one selected from the group consisting of water, an acid, a base, an enzyme, and the combinations thereof.

In accordance with an illustrative embodiment of the present disclosure, the reaction catalyst is recycled by collecting through the deposit removal unit.

In accordance with an illustrative embodiment of the present disclosure, the temperature of the downward reactor and the upward reactor is about from about 50° C. to about 300° C.

In accordance with an illustrative embodiment of the present disclosure, the downward reactor and the upward reactor are tilted.

Advantageous Effects of Invention

In accordance with the present disclosure, a high molecule polymer as an element of various biomass is continuously saccharified by using an apparatus in which a heating process, a decomposition process, and a saccharification process are continuously performed in a reactor, so that it is possible to effectively saccharify a great amount of marine algae and cellulosic biomass. Further, a time for saccharification is reduced, so that it is possible to reduce a processing cost.

BRIEF DESCRIPTION OF DRAWINGS

FIG. 1 is a schematic view of an apparatus for continuous saccharification of marine algae and cellulosic biomass in accordance with an illustrative embodiment of the present disclosure.

FIG. 2 is a schematic view of a reactor of an apparatus for continuous saccharification of marine algae and cellulosic biomass in accordance with an illustrative embodiment of the present disclosure.

FIG. 3 is a schematic view of a reaction unit of an apparatus for continuous saccharification of marine algae and cellulosic biomass in accordance with an illustrative embodiment of the present disclosure.

FIG. 4 is a schematic view of an apparatus for continuous saccharification of marine algae and cellulosic biomass in accordance with an illustrative embodiment of the present disclosure.

FIG. 5 is images of before a homogenization of a source (upper part) and after homogenization of the source (lower part) of an apparatus for continuous saccharification of marine algae and cellulosic biomass in accordance with an illustrative embodiment of the present disclosure.

BEST MODE FOR CARRYING OUT THE INVENTION

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "on" that is used to designate a position of one element with respect to another element includes both a case that the one element is adjacent to the another element and a case that any other element exists between these two elements.

Further, the term "comprises or includes" and/or "comprising or including" used in the document means that one or more other components, steps, operation and/or existence or addition of elements are not excluded in addition to the described components, steps, operation and/or elements unless context dictates otherwise. The term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Hereinafter, an apparatus for continuous saccharification of marine algae and cellulosic biomass in accordance with an illustrative embodiment will be explained in detail with reference to FIGS. 1 to 4. However, the present disclosure is not limited thereto.

Referring to FIGS. 1 to 3, an apparatus for continuous saccharification of marine algae and cellulosic biomass in accordance with an illustrative embodiment includes a source input unit 100, a reactor 200, a reaction unit including a downward reactor 300 and an upward reactor 400, a reactant liquid discharge unit 500, and a deposit removal unit 600.

A plurality of the source input unit 100 is included, and the source input unit is connected to a cushion tank to input a source into the reactor 200.

In an apparatus for continuous saccharification of marine algae and cellulosic biomass in accordance with an illustrative embodiment, red algae are transferred with a constant supply amount and uniformly react within the apparatus. Agitation is needed to prevent grains of the algae from sedimentation. A gas evaporated upwards can be managed and discharged at an appropriate pressure. It is necessary to control an appropriate temperature in the reactor and a flow rate and an internal pressure of a continuous saccharification reactor.

The source input unit 100 determines a solid/liquid ratio, a concentration of a catalyst, a temperature of a solution, and a speed of input.

The source input unit 100 is configured to supply a source. The source may include, but is not limited to, marine algae including micro-algae, terrestrial cellulosic biomass, or the combination thereof.

In an illustrative embodiment, the marine algae may include, but is not limited to, marine algae containing water or marine algae from which water is removed during a dehydration process. Further, the marine algae may include marine algae cut into a certain size in order to easily perform a saccharification process. The marine algae may include pre-treated marine algae in order to increase a process yield of the saccharification process. The pre-treatment may be employed without limitation from treatments typically used in the art to increase a process yield of a saccharification process. By way of example, the pre-treatment may include, but is not limited to, processing the marine algae with a swelling agent to make it easy for a catalyst and biomass to be in contact with each other during the saccharification process.

If necessary, the source input unit 100 may further include an agitator that prevents a tangle of the marine algae supplied into the reactor to easily supply the marine algae. The agitator may be employed without limitation from those typically used in the art to prevent a tangle of marine algae. By way of example, the source input unit 100 may include, but is not limited to, a stirring device.

A plurality of the reactor 200 may be included and the reactor 200 may be provided under the reaction unit including the downward reactor 300 and the upward reactor 400 so as to be connected thereto. The upward reactor 400 and the downward reactor 300 may be formed in a parallel unit in the order of the upward reactor 400 and the downward reactor 300 or the downward reactor 300 and the upward reactor 400. In the reactor 200, a source is mixed with a reaction catalyst, heated in certain temperature to convert a property, and then input into the reaction unit. As shown in FIG. 5, the input source is homogenized to form a paste (FIG. 5b).

The reactor 200 may include a spraying device, a driving unit, and a pressure control device 800.

The spraying device is configured to directly inject high-pressure steam into the reactor 200. The driving unit is configured to control a rotation speed in order to control a moving rate and a moving amount of the source. The pressure control device is configured to connect the source input unit 100 and the reactor 200, so that the marine algae can be supplied into the reactor while a high pressure is maintained in the reactor and the saccharification process can be continuously performed. Therefore, the apparatus for saccharification of marine algae in accordance with the present disclosure is a continuous saccharification apparatus capable of easily saccharifying a great amount of marine algae biomass.

Further, each reactor may include a jacket (not illustrated) capable of controlling a temperature to suppress production of a byproduct during the saccharification process and reduce a time for the saccharification process.

In an illustrative embodiment, the reactor 200, the downward reactor 300 and the upward reactor 400 are independent structures, and each reactor include a steam direct spray and the jacket to adjust the temperature.

In an illustrative embodiment, the saccharification process may be performed in the reactor 200 at a reaction temperature in a range of from about 50° C. to about 300° C., for example, about 100° C. to about 300° C., about 150° C. to about 300° C., about 200° C. to about 300° C., about 250° C. to about 300° C., about 50° C. to about 250° C., about 50° C. to about 200° C., about 50° C. to about 150° C., or about 50° C. to about 100° C. and a reaction pressure in a range of from about 1 bar to about 10 bar, for example about 5 bar to about 10 bar, or about 1 bar to about 5 bar for about 0.5 hours to about 5 hours, but the present disclosure is not limited thereto.

A connected path of the reactor 200, the downward reactor 300 and the upward reactor 400 is horizontal or tilted about 150°. Temperature, time and pressure of the reactor 200, the downward reactor 300 and the upward reactor 400 are adjusted separately.

The saccharification process may be performed by means of hydrolysis using the catalyst, for example, a hydrolysis catalyst and/or a hydrolysis enzyme. The saccharification process may include a direct saccharification process using marine algae as a source or an indirect saccharification process using cellulose and agar separated and/or extracted from the marine algae.

In an illustrative embodiment, the hydrolysis catalyst may be added to the marine algae supplied through the pressure control device so as to obtain only a monosaccharide or both of a monosaccharide and a polysaccharide. In this case, the polysaccharide can be converted into monosaccharides through hydrolysis using a hydrolysis catalyst or a hydrolysis enzyme. The monosaccharide or the polysaccharide may vary depending on a kind and an element of marine algae biomass. The polysaccharide may include one or more elements selected from a group including, for example, but not limited to, agar, cellulose, starch, carrageenan, alginic acid, and fibrin.

Further, the monosaccharide may include one or more elements selected from a group including, but not limited to, glucose, galactose, galactose derivatives, 3,6-anhydrogalactose, fucose, rhamnose, xylose, arabinose, and mannose.

The reactor 200, the downward reactor 300 and the upward reactor 400 may further include, but is not limited to, an impeller 900 by which upper and lower solutions are not mixed and the solutions moved along a moving direction together with solid matter in the solutions. A slope of the impeller 900 may be adjusted.

The reactor 200 may be provided in every direction at an angle in a range of from about 1° to about 90°, for examples, about 10° to about 90°, about 20° to about 90°, about 30° to about 90°, about 40° to about 90°, about 50° to about 90°, about 60° to about 90°, about 1° to about 80°, about 1° to about 70°, about 1° to about 60°, about 1° to about 50°, or about 1° to about 40° (FIG. 4). If the reactor 200 is provided to be tilted, a back slope of the reactor 200 faces upwards and downwards alternately and the reactor 200 can be unitized. The downward reactor 300 and the upward reactor 400 also may be provided in every direction at an angle in a range of from about 1° to about 90°, for examples, about 10° to about 90°, about 20° to about 90°, about 30° to about 90°, about 40° to about 90°, about 50° to about 90°, about 60° to about 90°, about 1° to about 80°, about 1° to about 70°, about 1° to about 60°, about 1° to about 50°, or about 1° to about 40° (FIG. 4).

In an illustrative embodiment, a screen may be provided at a specific column to extend a reaction time of the solid matter and delay a movement of the solid matter.

If necessary, a device for circulating and supplying cooling water to the outside of the reactor may be further provided in order to prevent the reactor 200 from being overheated, but the present disclosure is not limited thereto.

The reactant liquid discharge unit 500 is configured to maintain a speed of discharged to be equal to the speed of input.

The deposit removal unit 600 is configured to supply steam to a lower part of the reactor 200 and remove a deposit in the reactor 200. The reaction catalyst may be recycled from the deposit collected by the deposit removal unit 600.

The apparatus for continuous saccharification of marine algae and cellulosic biomass in accordance with the present disclosure can be controlled by a control system, which is not illustrated, connected to the apparatus. The control system may control, for example, a speed of input of the marine algae and terrestrial cellulosic biomass, a rotation speed of a screw, a temperature and/or a pressure in the reactor, and a supply amount of the catalyst.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

EXPLANATION OF CODES

100: Source input unit
200: reactor
300: Downward reactor
400: Upward reactor
500: Reactant liquid discharge unit
600: Deposit removal unit
700: Cushion tank
800: Pressure control device
900: Impeller

The invention claimed is:

1. An apparatus for performing continuous saccharification of biomass, the apparatus comprising:
    a source input unit for supplying a source of the biomass;
    a first reactor in fluid communication with the source input unit for receiving the source from the source input unit;
    a reaction unit including a downward reactor in fluid communication with the first reactor through an inlet located near a top of the downward reactor to receive the source from the first reactor and configured to move the source downwardly from the inlet, and an upward reactor in fluid communication with the downward reactor through an outlet located near a bottom of the downward reactor to receive the source from the downward reactor and configured to move the source upwardly from the outlet;
    a reactant liquid discharge unit provided near a top of the upward reactor for discharging the source from the upward reactor; and
    a deposit removal unit provided near a bottom of the downward reactor for removing deposits from the source collected at the bottom of the downward reactor;
    wherein an axis of the downward reactor and an axis of the upward reactor are tilted at a predetermined angle away from 90°.

2. The apparatus of claim 1, wherein the source includes marine algae, terrestrial cellulosic biomass, or a combination thereof.

3. The apparatus of claim 1, wherein the source includes marine algae containing water or marine algae from which water is removed by a dehydration process.

4. The apparatus of claim 1, wherein the source input unit further includes an agitator.

5. The apparatus of claim 1, wherein the first reactor comprises a spraying device, a driving unit, and a pressure control device.

6. The apparatus of claim 5, wherein the spraying device is configured to directly inject high-pressure steam into the first reactor.

7. The apparatus of claim 1, wherein each of the downward reactor and the upward reactor further includes an impeller.

8. The apparatus of claim 7, wherein a slope of each of the impellers are set to enable the source to move in a reaction direction of the downward reactor and the upward reactor.

9. The apparatus of claim 1, wherein the source is mixed with a reaction catalyst in the first reactor.

10. The apparatus of claim 9, wherein the reaction catalyst is selected from the group consisting of water, an acid, a base, an enzyme, and the combinations thereof.

11. The apparatus of claim 9, configured such that the reaction catalyst is collected through the deposit removal unit and recycled.

12. The apparatus of claim 1, configured to maintain the temperature of the downward reactor and the upward reactor at about from about 50° C. to about 300° C.

* * * * *